United States Patent [19]

Alexander

[11] 4,423,327
[45] Dec. 27, 1983

[54] FOOD STUFF MATURITY SENSING AND INSPECTION APPARATUS

[76] Inventor: Richard Alexander, 5333 Sepulveda Blvd., No. 3, Culver City, Calif. 90230

[21] Appl. No.: 949,944

[22] Filed: Oct. 10, 1978

[51] Int. Cl.³ ............................................. G01N 23/00
[52] U.S. Cl. ............................. 250/358.1; 250/359.1; 378/54
[58] Field of Search ................... 250/358 R, 359, 360

[56] References Cited

U.S. PATENT DOCUMENTS 2,706,789   4/1955   Hughes ........................... 250/358 R
3,594,579   7/1971   Garrett et al. ....................... 250/360

Primary Examiner—Janice A. Howell
Attorney, Agent, or Firm—Michael A. Painter

[57] ABSTRACT

Food stuff maturity sensing and inspection apparatus particularly suited for sensing the maturity of head lettuce and the like. The sensing apparatus utilizes an x-ray radioactive source for directing radiation toward the growing vegetable, with an x-ray detector on the opposite side of the vegetable detecting the attenuation of the radiation caused by the density of the vegetable therebetween. The normal inverse exponential attenuation of radiation caused by an object between a source and sensor is effectively linearized by the use of a simple high accuracy logarithmic count rate circuit. The relatively low energy of x-ray emitters such as Cadmium 109 results in greater rates of change of the detected signal for a given change of density of the vegetables in the path of the radiation. The technique may also be used to detect foreign materials harvested with food crops from the density differences detected by the apparatus.

6 Claims, 4 Drawing Figures

FOOD STUFF MATURITY SENSING AND INSPECTION APPARATUS

BACKGROUND OF THE INVENTION

1. Field of the Invention

The present invention relates to the field of harvesting apparatus, and more particularly to apparatus for sensing the maturity of vegetables and/or the existance of contaminants in growing and harvested food stuffs.

2. Prior Art

Certain food stuffs such as wheat are harvested based upon the average maturity of the crop or field. Other food stuffs, however, often are selected for harvesting at a particular picking based upon their size, weight, etc. One such food stuff, by way of specific example, is lettuce, wherein the chief criteria for appropriate maturity is the density of the head. In that regard, different heads, even in the same row and thus supposedly subjected to the same growing conditions, will mature at different times so that the best crop yield will be obtained through the use of multiple pickings, selecting only the appropriately mature heads each time. While the size of the heads are visually perceivable and could be optically detected automatically, size for certain food stuffs such as lettuce is not an adequate indicator of density, and thus is not an appropriate basis for determining the appropriate picking time. Thus, in manual harvesting, the field hand will normally lightly squeeze the lettuce head to determine suitability for picking, the experienced field hand exhibiting considerable expertise in the judgements made.

It has been recognized that mechanical (automatic) lettuce pickers could be used to harvest a lettuce crop at a substantially lower cost, provided some appropriate method of automatically testing the lettuce head for density could be implemented so that individual picking decisions could be made as the harvesting machine is moved along the lettuce rows.

One method and apparatus for automatic measurement of size and density of produce is disclosed in U.S. Pat. No. 3,594,579. That system utilizes Americium 241 radioactive isotope as a source of gamma rays for size and density selection. The gamma ray source is collimated into a pencil beam which passes through the lettuce head and is detected on the other side thereof by a photomultiplier. By observing the count rate decrease at the center of the head, an attenuation criteria for a fully mature head may be established. That system also contemplates the measurement of a head diameter based upon the distance along the row over which the radiation attenuation was substantial because of the existance of the head between the source and detector.

The gamma ray isotope system just described is relatively simple, but has certain very serious drawbacks. In particular, approximately 30 millicuries of Americium 241 is required, representing a fairly large amount of the very toxic isotope. Although the source is sealed, unexpected accidents could result in the loss of containment which would pose a very serious health hazard in food stuffs, as gamma ray emitters such as Americium 241 are associated with alpha particle emitters and tend to be bone seekers if ingested. As a result, controlling agencies are quite worried about granting licenses for gamma ray emitters for use in the crop fields because of the possible consequences of an unexpected event.

P. A. Adrian and D. H. Lenker have used a maturity sensing system having an x-ray generator as an x-ray source and a pair of silicon photodiodes as detectors. The detectors are arranged such that one photodiode sees an unattenuated beam while the other sees a beam attenuated by the presence of a lettuce head. The difference in the current detected in such a system can be correlated to maturity for the produce being tested. (A more complete description of that system may be found in a paper entitled "A Selective Crisphead Lettuce—Harvest System" by D. H. Lenker, et al., presented at the 1972 Annual Meeting of the American Society of Agricultural Engineers, Hot Springs, Arkansas, as paper number 72-146). The foregoing system operated well in terms of accuracy of the measurements but was subject to the difficulties commonly encountered with x-ray generators in general. In particular, x-ray tubes have a limited and unpredictable life, are shock sensitive and have (with their auxiliary high voltage power supply) failure modes which can cause excessive radiation output. In addition, their output can vary with temperature, supply voltage and life, requiring the reference channel hereinbefore referred to to normalize the unattenuated beam. The particular generator used for those tests was a converted World War II surplus dental x-ray unit no longer available on the market. In such a system the total flux of x-rays is quite high due to the lack of sensitivity in the detector used. In addition, the pulse nature of the x-ray beam requires additional circuit complexity with the attendant cost and maintenance problems. Of course, that system, as well as the gamma ray system hereinbefore described, had no provision for linearizing the density versus voltage output of the electronics, resulting in a signal characteristic which is difficult to interpret by the untrained eye, and not the most desirable for automatic decision making purposes, as it is very awkward to present to untrained personnel for changing the acceptance level in the field. This problem may be particularly illustrated by noting that the attenuation of a gamma or x-ray beam passing through any material may be expressed as $$R = R_o e^{-\mu \rho x}$$

Where
  R is the attenuated beam in photons/sec.
  $R_o$ is the unattenuated beam in photons/sec.
  $\mu$ is the attenuation coefficient of the material in cm$^2$/gr
  $\rho$ is the density of the material in gr/cm$^3$
  x is the thickness in cm Thus if the $\mu$ is constant and the electronics respond linearly to the attenuated count rate, the output increases proportionally to the reciprical of the density-thickness product, i.e.

$$\text{output voltage} \propto 1/e^{\rho x}$$

If, on the other hand, the electronics could extract the log of R (as in the present invention), the output signal would be $$V_1 \propto \log(e^{-\mu \rho x}) = -\mu \rho x$$

BRIEF SUMMARY OF THE INVENTION

Vegetable maturity sensing apparatus particularly suited for sensing the maturity of head lettuce and the like. The sensing apparatus utilizes an x-ray radioactive source for directing radiation toward the growing vegetable, with an x-ray detector on the opposite side of the vegetable detecting the attenuation of the radiation caused by the density of the vegetable therebetween. The normal inverse exponential attenuation of radiation caused by an object between a source and sensor is effectively linearized by the use of a simple high accuracy logarithmic count rate circuit. The relatively low energy of x-ray emitters such as Cadmium 109 results in greater rates of change of the detected signal for a given change of density of the vegetables in the path of the radiation. The technique may also be used to detect foreign materials harvested with food crops from the density differences detected by the apparatus.

DETAILED DESCRIPTION OF INVENTION

Figure 1:
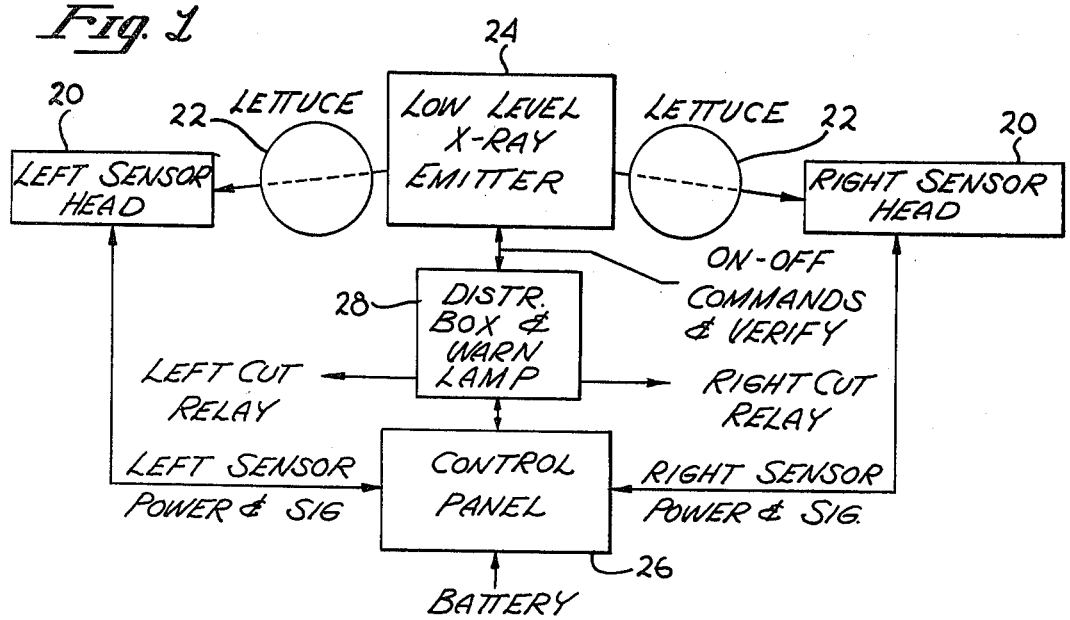
FIG. 1 is a block diagram of a typical lettuce maturity sensing system embodying the present invention.
Figure 2:
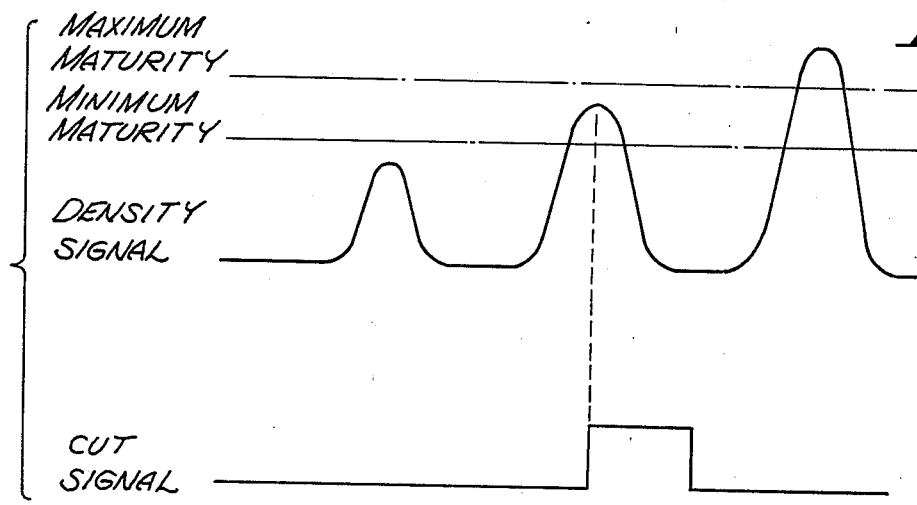
FIG. 2 is an illustration of the sensing characteristics of the preferred embodiment.

First referring to FIG. 1, a block diagram of a preferred form of maturity sensor, specifically for purposes of explanation only a lettuce maturity sensor, may be seen. This system is composed of five basic inter-coupled elements. These elements include left and right sensor heads 20 each disposed adjacent one of a pair of rows of head lettuce (exemplified by the lettuce heads 22) with a central low level x-ray emitter 24 disposed between the two lettuce rows so as to direct columnated x-ray radiation in generally opposite directions toward the lettuce heads in the two adjacent rows from a common radiation source. Thus, as the automatic picker on which the maturity sensor is mounted at an appropriate level is advanced along the rows, each lettuce head of both rows passes through an x-ray beam that is detected by the sensor heads. Individual photons are detected by the sensors and converted to a high level pulse which is sent to a control panel 26 (to be subsequently described in greater detail). The control panel converts the pulse rate, which of course is dependent upon the attenuation of the radiation by each lettuce head, to a voltage proportional to the density. This voltage is compared to a preselected minimum and maximum voltage representing a lower level of minimum maturity and an upper level of maximum maturity. When the head is within the acceptance window a cut signal is generated and sent to the appropriate cut relay through a distribution box 28 controlling a mechanical cutter, the specific details of which are not the subject of the present invention. As shall subsequently be seen, the control panel senses the increasing density signal as a head passes between the low level x-ray emitter and the respective sensor head, and when that signal peaks, compares that peak with the preset (though adjustable) maximum and minimum maturity signals to provide the cut signal. Thus, as may be seen in FIG. 2, the density signal received from a particular sensor head will in general fall into one of three categories, specifically in the sequence illustrated in FIG. 2, signals characteristic of an immature, a mature and an overly mature lettuce head when compared to the preset maturity levels. When a signal peaks between the two maturity limits a cut signal is immediately generated, remaining for a sufficient length of time to execute the cut operation before changing to the initial level before the next head passes the sensor.

Figure 3:
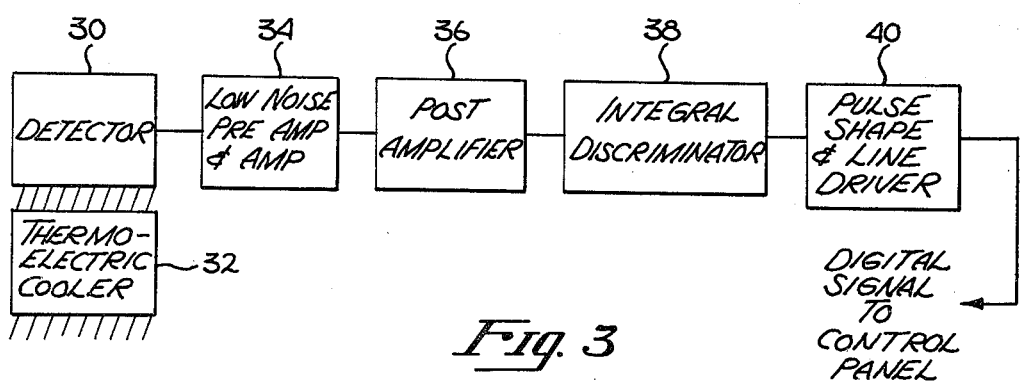
FIG. 3 is a block diagram of a typical channel of the preferred embodiment.

Now referring to FIG. 3, a block diagram of a sensor head may be seen. In the preferred embodiment, the detector 30 is a silicon x-ray detector having a sufficient area and depletion depth to record a statistically significant number of x-rays in the beam impinging on the detector after being attenuated by a mature lettuce head. In order to limit the thermal noise of a detector to a point well below the expected (22 keV) signal level during field operations, the detector 30 is mounted on a thermoelectric cooler 32, heat sinked to the frame of the harvester. The detector output is coupled to a low noise charge sensitive amplifier 34, with a second stage of amplification being provided by the post amplifier 36 before the voltage discriminator 38 selects only those pulses representing an x-ray interaction in the detector, rejecting the lower level pulses due to noise. The discriminator pulse is shaped by the pulse shape and line driver 40 to the appropriate amplitude and duration for further counting and buffered for transmission to the control console. Accordingly, the output from the sensor head is a train of pulses of predetermined amplitude and duration, randomly occurring in time and having an average repetition rate ranging from the maximum rate characteristic of the source and sensor system, to reduced rates responsive to the maturity of the lettuce head aligned with the source and detector.

The control panel 26 of FIG. 1 generally contains the peripheral and supporting electronic equipment for the system as well as the signal processing circuits to derive the cut signal. Thus, located within the control panel are low voltage and detector bias power converters, lamp drivers, calibration controls, the low level x-ray emitter control and internal diagnostic circuits, all of which are generally well known in the prior art and therefore not further described herein.

Figure 4:
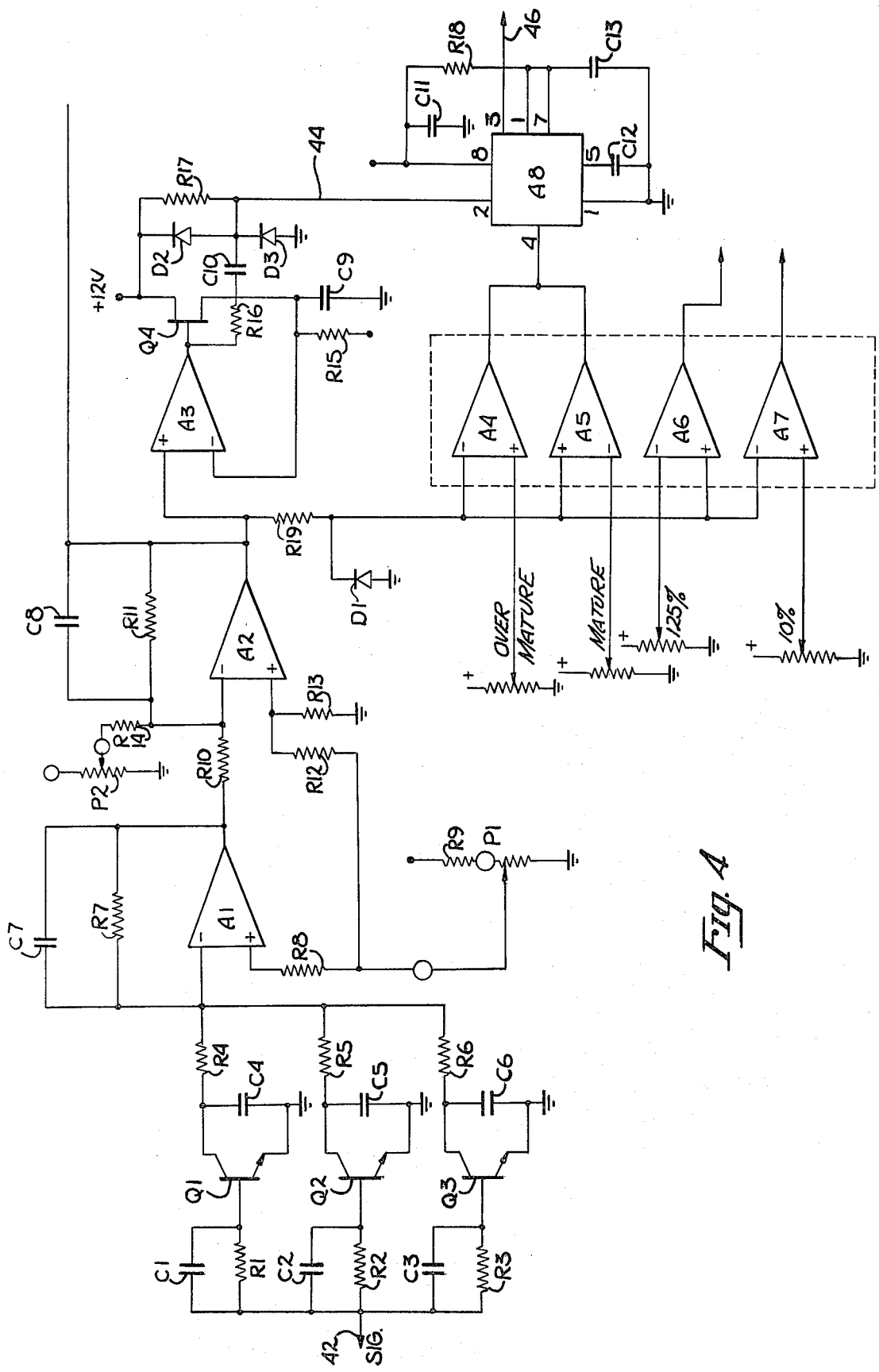
FIG. 4 is a circuit diagram of the processing circuitry for each channel.

A schematic diagram of a typical signal processing circuit may be seen in FIG. 4, two such circuits being used in the system of the preferred embodiment to derive the left and right cut signals from the left and right sensors respectively. Each pulse in the incoming signal on line 42 is applied to the base of transistors Q1, Q2 and Q3 through the circuits comprised of R1 and C1, R2 and C2 and R3 and C3 respectively. Each pulse turns on in parallel, transistors Q1, Q2 and Q3 for a period of time sufficient to remove the charge on capacitors C4, C5 and C6. These capacitors in the preferred embodiment have values of 680 picofarads, 0.0068 microfarads and 0.068 microfarads respectively, so as to increase geometrically in decade jumps. (Resistors R1, R2 and R3 are each 100K resistors, with capacitors C1, C2 and C3 being 68 picofarads, 680 picofarads and 0.01 microfarads respectively). Operational amplifier A1 has its negative input coupled to the capacitors C4, C5 and C6 through resistors R4, R5 and R6 respectively, with feedback of the amplifier output being provided to the negative input through resistor R7 and capacitor C7. The positive input of amplifier A1 is a reference voltage provided by resistors R8 and R9 and potentiometer P1 coupled between ground and a positive reference voltage, with the same network also providing a lower reference voltage to amplifier A2 through a voltage divider comprised of resistors R12 and R13. After each pulse on line 42 during which time capacitors C4, C5 and C6 are discharged, a recharge current for these capacitors is provided by the feedback circuit R7 and C7, so that the output voltage of the amplifier A1 is proportional to the logarithm of the input count rate. In that regard, the potentiometer P1 serves as a calibration for the system, since the logarithmic response of the circuit is directly proportional to the recharge voltage for capacitors C4 through C6, which in turn is equal to the input voltage on the positive terminal of the amplifier A1. (The coupling of a portion of the calibration voltage from potentiometer P1 to the positive input of amplifier A2 effectively cancels the output level dependence of amplifier A1 on the calibration adjustment). The theoretical and experimental basis for this circuit is presented in a paper entitled "A Simple High Accuracy Logarithmic Count Rate Circuit Suitable for Space Craft Use", by R. M. Alexander and I. M. Green, IEEE Transactions on Nuclear Science, NS-16 No. 1, Feb. 1969.

The output of amplifier A1 is coupled through resistor R10 to amplifier A2, which standardizes the signal such that 0 volts on the output of amplifier A2 is equivalent to the unattenuated beam, and approximately 4 volts is equivalent to a totally attenuated beam. In that regard, a 0 adjustment is provided through potentiometer P2 to provide a nulling capability for the channel. (Resistors R7 and R11 provide the feedback for the amplifiers A1 and A2 respectively, with capacitors C7 and C8 in conjunction with the respective resistors forming a two pole smoothing filter for the log count rate meter formed by the hereinbefore described circuit).

Devices A4, A5, A6 and A7 comprise a quad voltage comparator which establishes sensor ready criteria, detects gross radioactive material leaks if they should occur, and establishes the criteria for the selection of a head of lettuce to be cut. In particular the output of amplifier A2 is coupled through resistor R19 to the negative inputs of comparators A4, A6 and A7 and to the positive input of comparator A6, with diode D1 providing reverse voltage protection to the integrated circuit comparators. The positive input for comparator A4 is coupled to an adjustable voltage establishing the over mature level limit, with the negative input of comparator A5 being coupled to an adjustable voltage representing the mature level input. Thus when the output voltage of amplifier A2 is below the selected level of maturity, a positive differential is applied to comparator A4 and a negative differential is applied to comparator A5. Also, when the output of amplifier A2 exceeds the over mature level, comparator A4 has a negative differential and comparator A5 has a positive differential. However, when the output of amplifier A2 is between the mature level and the over mature level, both comparators A4 and A5 have a positive differential, thereby providing a signal to the one-shot multivibrator A8. In particular, device A8 in the preferred embodiment is a type 555 timer (as manufactured by Motorola and many others) connected with the pin identifications as shown. Amplifier A3 has its positive input coupled to the output of amplifier A2 with feedback to the negative input being provided through transistor Q4, resistor R15 and capacitor C9. So long as the output of amplifier A2 is increasing, a positive differential is applied to amplifier A3 so that capacitor C9 is charging through the transistor Q4. However, since the capacitor C9 and resistor R15 (together with any input current required by amplifier A3) provide a relatively long time constant on the discharge of capacitor C20 whenever the output voltage of amplifier A2 peaks and starts dropping, capacitor C9 holds the negative input to the amplifier A3 at the previous higher level, thereby resulting in a negative differential on amplifier A3 so that its output immediately goes low. This is coupled through resistor R16 and capacitor C10 to the one-shot A8, with diodes D2 and D3 providing voltage protection and quick discharging of capacitor C10 when the output of amplifier A3 again goes high, and with resistor R17 controlling the pulse wave shape applied to the one-shot through line 44. Thus, the outputs of comparators A4 and A5 are effectively used as an enable signal of the one-shot A8, with the trigger being applied on line 44 by the peak detection of amplifier A3 and transistor Q4 and associated circuitry. (The remaining components C11 and C12, C13 and R18, among other things, define the pulse width of the output of the one-shot to provide the cut signal output pulse shown in FIG. 2 on line 46).

The negative input of comparator A6 is coupled to a reference voltage representing a voltage output from amplifier A2 which is 125% of the output of an operational system for an unattenuated radiation beam, while the positive input of comparator A7 is coupled to a reference voltage representing 10% of the output characteristic of an unattenuated radiation source. Thus, under normal operating conditions, even for over mature lettuce heads, the radiation received by the detectors will exceed 10% but of course not exceed the 100% level, thereby falling within the band determined by the reference for comparators A6 and A7 to provide a negative differential thereto. However, in the event of malfunction in the radiation source, one of these two limits will normally be exceed. In particular, if the radiation source fails to open on receipt of the control signal thereto or the radioactive material has leaked out and is no longer in the vicinity, then the signal received by the detectors should be less than 10% of the expected maximum signal, thereby providing a positive output signal on comparator A7 for signaling purposes. (The radiation container comprises a substantially radiation proof enclosure having openings normally covered by shutters, but which shutters are withdrawn by appropriate electrical control signals to provide the desired columnated beam through the openings). Similarly, if the radioactive source has leaked out with a substantial portion thereof at or around the enclosure and/or detector, the output signal may exceed the normally expected limit thereby triggering comparator A6 to signal such an occurrence. In that regard, it will be noted that in the event a dense foreign object passes between the radiation source and a detector, such as by way of example a large rock, etc. this too may attenuate the radiation beam an unusual amount thereby also triggering the comparator A7.

In the preferred embodiment the radiation source contains 10 millicuries of Cadmium 108, an amount which may be buried for disposal, yet which with an appropriate sensor, particularly a cooled sensor, will provide a statistically valid output. Obviously in other applications the size of the source may be varied based on the nature of the produce, spacing of the source and detector, etc. though sources larger than 100 millicuries would generally be unnecessarily large, and sources less than 1 millicurie generally would not provide a statistically significant detector output.

There has been described herein one particular embodiment of a new and unique vegetable maturity sensing system, that embodiment being specifically adapted to the sensing of lettuce maturity to provide a cut signal for automatic harvesting equipment. Obviously, however, the system may be readily adapted to sense maturity of other foods stuffs as desired. In that regard, it will be noted that the exemplary embodiment described herein is one intended generally for the detection of the density of produce as an indication of maturity, though it will be immediately obvious that the invention may readily be utilized to detect the presence of foreign matter such as stones, etc. in harvested food stuffs such as, by way of example, wheat, by setting appropriate bounds in the radiation attenuation expected for uncontaminated wheat. Thus, while the preferred embodiment of the present invention has been disclosed and described in detail herein, it will be understood by those skilled in the art that various changes in form and detail may be made therein without departing from the spirit and scope of the invention.

I claim:
1. A food stuff inspecting system comprising:
   (a) a cadmium 109 source of low level x-ray radiation for directing radiation through produce in an amount inversely exponentially responsive to the density of the food stuff;
   (b) a radiation detector for providing a detector signal responsive to emission incident thereto, said detector being cooperatively disposed with respect to said radiation source to receive emission therefrom passing through the food stuff; and
   (c) signal processing means for processing said detector signal to determine occurrence of a predetermined characteristic in the food stuff, said signal processing means comprising:
      (1) first electrical translation means for receiving said detection signal and outputting a signal responsive thereto;
      (2) a logarithmic amplifier, the input thereof being connected to the output of said electrical translation means, the output of said logarithmic amplifier being the logarithm of the signal output from said electrical translation means;
      (3) second electrical translation means for standardizing the detection signal, the input of said second electrical translation means being connected to the output of said logarithmic amplifier;
      (4) a first comparator having first and second inputs and a comparator output, said first input being connected to the output of said second electrical translation means, the second input being connected to means for producing an electrical signal responsive to a first state of the food stuff being inspected;
      (5) a second comparator having first and second inputs and a comparator output, said first input being connected to the output of said second electrical translation means, the second input being connected to means for producing an electrical signal responsive to a second state of the food stuff being inspected, the comparator outputs of said first and second comparators being connected to one another whereby the connected comparator outputs of said first and second comparators produce a signal output only when the signal output from said second electrical translation means is intermediate the levels of the electrical signals responsive to the first and second states of the food stuff being inspected;
      (6) feedback amplifier means for detecting a change in the polarity of the electrical signal input thereto and producing a linear output signal responsive thereto, said feedback amplifier means having first and second inputs, said first input connected to the outut of said second electrical translation means, the linear output signal of said feedback amplifier means being coupled to the second input thereof; and
      (7) pulse means for producing a signal responsive to an acceptable state of the food stuff being inspected, said pulse means being connected to the output of said feedback amplifier and said first and second comparators whereby the output signal of said pulse means is responsive to the output signals of said feedback amplifier and said first and second comparators.

2. The system of claim 1 wherein said source of radiation is a radioactive source.

3. The system of claim 1 wherein said radiation source comprises Cadmium 109 in the range of 1 to 100 millicuries.

4. The system of claim 1 wherein said radiation source comprises approximately 10 millicuries of Cadmium 109.

5. A food stuff inspecting system as defined in claim 1 wherein said signal processing means comprises:
   (a) first electrical translation means for receiving said detection signal and outputting a signal responsive thereto;
   (b) a logarithmic amplifier, the input thereof being connected to the output of said electrical translation means, the output of said logarithmic amplifier being the logarithm of the signal output from said first electrical translation means;
   (c) second electrical translation means for standardizing the detection signal, the input of said second electrical translation means being connected to the output of said logarithmic amplifier;
   (d) a first comparator having first and second inputs and a comparator output, said first input being connected to the output of said second electrical translation means, the second input being connected to means for producing an electrical signal responsive to a first state of the food stuff being inspected;
   (e) a second comparator having first and second inputs and a comparator output, said first input being connected to the output of said second electrical translation means, the second input being connected to means for producing an electrical signal responsive to a second state of the food stuff being inspected, the comparator outputs of said first and second comparators being connected to one another whereby the connected comparator outputs of said first and second comparators produce a signal output only when the signal output from said second electrical translation means is intermediate the levels of the electrical signals responsive to the first and second states of the food stuff being inspected;
   (f) feedback amplifier means for detecting a change in the polarity of the electrical signal input thereto and producing a linear output signal responsive thereto, said feedback amplifier means having first and second inputs, said first input connected to the output of said second electrical translation means, the linear output signal of said feedback amplifier means being coupled to the second input thereof; and
(g) pulse means for producing a signal responsive to an acceptable state of the food stuff being inspected, said pulse means being connected to the output of said feedback amplifier and said first and second comparators whereby the output signal of said pulse means is responsive to the output signals of said feedback amplifier and said first and second comparators.

6. A food stuff inspecting system comprising:
(a) a source of low level x-ray radiation for directing radiation through produce in an amount inversely exponentially responsive to the density of the food stuff;
(b) a radiation detector for providing a detector signal responsive to emission intimate thereto, said detector being cooperatively disposed with respect to said x-ray radiation source to receive emission therefrom passing through the food stuff; and
(c) a signal processor for processing the detection signal comprising:
  (i) first electrical translation means for receiving said detection signal and outputting a signal responsive thereto;
  (ii) a logarithmic amplifier, the input thereof being connected to the output of said electrical translation means, the output of said logarithmic amplifier being the logarithm of the signal output from said first electrical translation means;
  (iii) second electrical translation means for standardizing the detection signal, the input of said second electrical translation means being connected to the output of said logrithmic amplifier;
  (iv) a first comparator having first and second inputs and a comparator output, said first input being connected to the output of said second electrical translation means, the second input being connected to means for producing an electrical signal responsive to a first state of the food stuff being inspected;
  (v) a second comparator having first and second inputs and a comparator output, said first input being connected to the output of said second electrical translation means, the second input being connected to means for producing an electrical signal responsive to a second state of the food stuff being inspected, the comparator outputs of said first and second comparators being connected to one another whereby the connected comparator outputs of said first and second comparators produce a signal output only when the signal output from said second electrical translation means is intermediate the levels of the electrical signals responsive to the first and second states of the food stuff being inspected;
  (vi) feedback amplifier means for detecting a change in the polarity of the electrical signal input thereto and producing a linear output signal responsive thereto, said feedback amplifier means having first and second inputs, said first input connected to the output of said second electrical translation means, the linear output signal of said feedback amplifier means being coupled to the second input thereof; and
  (vii) pulse means for producing a signal responsive to an acceptable state of the food stuff being inspected, said pulse means being connected to the output of said feedback amplifier and said first and second comparators whereby the output signal of said pulse means is responsive to the output signals of said feedback amplifier and said first and second comparators.

* * * * *